United States Patent [19]
Schneider

[11] 3,969,411
[45] July 13, 1976

[54] PROCESS FOR N-ALKYLATING AROMATIC AMINES

[75] Inventor: Joachim Schneider, Krefeld, Germany

[73] Assignee: Bayer Aktiengesellschaft, Leverkusen, Germany

[22] Filed: Sept. 11, 1974

[21] Appl. No.: 505,115

[30] Foreign Application Priority Data
Sept. 28, 1973  Germany............................ 2348738

[52] U.S. Cl.................................. 260/577; 260/571; 260/573; 260/574; 260/576
[51] Int. Cl.$^2$.................... C07C 87/50; C07C 87/54
[58] Field of Search ............ 260/577, 576, 574, 571, 260/573

[56] References Cited
UNITED STATES PATENTS

| | | | |
|---|---|---|---|
| 2,073,671 | 3/1937 | Andrews......................... | 260/577 X |
| 2,991,311 | 7/1961 | Thoma............................... | 260/577 |

*Primary Examiner*—Helen M. S. Sneed
*Attorney, Agent, or Firm*—Burgess, Dinklage & Sprung

[57] ABSTRACT

N-alkylated aromatic amines are prepared by heating an aromatic amine together with a lower aliphatic alcohol in the presence of from 0.01 to 1.0 mol of phosphoric acid per nitrogen equivalent at a temperature in the range of from 150°–280°C. Thereafter, the liquid phases that form are separated to isolate the N-alkylated aromatic amine.

7 Claims, No Drawings

PROCESS FOR N-ALKYLATING AROMATIC AMINES

BACKGROUND

This invention relates to a particularly advantageous process for the liquid phase N-alkylation of an aromatic amine by reacting the amine with an alcohol in the presence of phosphoric acid.

It is known that aniline can be alkylated by passing a mixture of methanol and aniline through hot concentrated phosphoric acid (DT-PS No. 1,031,796). One disadvantage of this process is that N,N-dialkyl compounds, especially those with alkyl radicals other than the methylradical, are difficult to obtain on a commercial scale in this way. Other disadvantages are that the product always contain a considerable quantity of N-monoalkyl compound as a secondary product in addition to the N,N dialkyl compounds, and that the catalyst used loses activity after prolonged use.

SUMMARY

It has now been found that the N-alkylation of an aromatic amine can be carried out particularly easily and economically by heating the aromatic amine with a lower aliphatic alcohol for example containing 1 to 3 carbon atoms, in the presence of 0.01 to 1.0 mol of phosphoric acid per nitrogen equivalent, and separating the liquid phases formed to isolate the alkylated aromatic amine.

DESCRIPTION

The process according to the invention can be carried out with any aromatic amine accessible to alkylating reactions on the nitrogen (Kirk-Othmer, Encyclopedia of Chemical Technology, Vol. 2, page 420), provided they are stable in the presence of phosphoric acid and at the temperature applied in the process according to the invention. It is particularly suitable to use aromatic amines of the aniline and diphenylamine series, including the corresponding nucleus-substituted derivatives. Generally, the only qualification which has to be made in regard to substitution is that the substituents should not be and/or contain groups and/or radicals of the kind which themselves react under the conditions of the process according to the invention. This qualification applies especially to aromatic diamines, whose unsubstituted amino groups substitute the same nucleus, but not to those which are substituted in various nuclei, such as, for example, diaminodiphenyls.

The following are mentioned as examples of substituents which can substitute the aromatic amines: halogen (e.g. fluorine, bromine, chlorine, or iodine), preferably fluorine, chlorine and bromine, lower alkyl-, alkoxy- and alkylmercapto-radicals with 1 to 4, preferably with 1 to 2 carbon atoms. When the amine is aniline and its derivatives, phenyl which may itself be optionally substituted by the aforementioned substituents may be the substituent.

The aromatic amines can of course also be repeatedly substituted by the aforementioned substituents, in particular halogen, alkyl and alkoxy, disubsitution by identical or different substituents being particularly applicable.

The most important aromatic amines which can be used correspond to the formula:

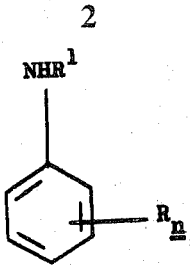

in which:
R represents halogen, a lower alkyl-, alkoxy- or alkylmercapto-radical or a phenyl radical which can be substituted by a lower alkyl-, alkoxy- or alkylmercapto-radical;
$R^1$ represents hydrogen, a lower alkyl radical or a phenyl or aminophenyl radical which can be substituted by a lower alkyl-, alkoxy- or arylmercapto-radical; and
$n$ represents 0, 1, 2 or 3.

Aromatic amines of the above formula in which:
R represents chlorine, methyl or ethyl,
$R^1$ represents methyl, ethyl, phenyl, methoxyphenyl, ethoxyphenyl or aminophenyl, and
$n = 0$, 1 or 2, especially 0 or 1,
are preferably used as starting material.

The following are particular examples of the amines used: aniline, o-, m-, p-tolidine, the xylidines, chlorine-substituted anilines, 2- or 4-methoxydiphenylamine, 4-ethoxydiphenylamine or 2-aminodiphenyl.

Lower aliphatic alcohols, preferred alkyl alcohols, with 1 to 3 carbon atoms, especially methanol and ethanol, are preferably used in the alkylation process. Alkylation is generally carried out with an excess of alcohol. The excess unreacted alcohol can of course be re-used, optionally after removal of the water present in it which is formed during the reaction The reaction temperature is in the range from 150° to 280°C, preferably in the range from 160° to 240°C and more particularly in the range from 180° to 210°C. Alkylation in the nucleus of the aromatic amine can thus be avoided.

The development of a second liquid phase in the presence of the alkylation products is essential for carrying out the process according to the invention. The second phase is obtained by limiting the quantity of concentrated phosphoric acid used to 0.01 to 1 mol, preferably to 0.05 to 0.5 mol, per nitrogen equivalent. The upper limit of the quantity of phosphoric acid which can then be used is governed by the aromatic amine to be alkylated. If necessary, it can readily be determined by a preliminary test whether the development of the two liquid phases essential to the invention actually takes place for the amine to be alkylated.

The quantity of phosphoric acid used can also determine the reaction velocity. In the above range, the reaction velocities obtained with relatively large quantities of phosphoric acid will be higher than those obtained with relatively small quantities.

The concentration of phosphoric acid used in the process according to the invention is not important, because the water present in it, if any, is removed by distillation during the reaction. It is possible to use commercial-grade aqueous phosphoric acid containing from 50 to 100 % by weight of $H_3PO_4$. It is preferred to use readily available, concentrated phosphoric acid, i.e. standard commercial phosphoric acid with an $H_3PO_4$ concentration of 85 to 89 % by weight. Metaphosphoric acid and polyphosphoric acid can also be used.

The phosphoric acid which is used as a catalyst forms with the aromatic amine a salt whose melting point is generally below the reaction temperature. If, however, a salt of phosphoric acid and the amine to be alkylated is formed which melts at a temperature above the reaction temperature, so preventing the formation of two liquid phases, the alkyl or dialkyl compound to be prepared can be added to the mixture in order to reduce the melting point and hence to promote the development of liquid phases. The advantage of this is that there is no need to introduce into the reaction mixture other foreign substances which would have to be subsequently removed, often with considerable difficulty. The necessary quantity may optionally be readily determined by a preliminary test. However, an excess is harmless. In general, it has proved to be advantageous to add approximately 10 – 50 % by weight, based on the amine used.

To carry out the process according to the invention, a mixture of the aromatic amine to be alkylated and the selected quantity of phosphoric acid can be introduced into an upright reaction tube which is wider at its upper end in order to separate the gas and liquid phase and to prevent foaming. The alcohol is then introduced at the lower end of the reaction tube either in liquid or in gaseous form at the required reaction temperature. The gaseous products escaping from the reaction mixture (such as excess alcohol and the water formed during the reaction) are passed through an attachment connected to the wider upper end of the reaction tube (for example in the form of a column of a condenser kept at a suitable temperature) in such a way that the high-boiling nitrogen-containing aromatic compounds are condensed and returned to the reactor, whilst the excess alcohol and the water of reaction leave the attachment, for example overhead, in the gas phase and are then condensed, or alternatively actually condense in the attachment and are suitably removed in a side stream, so that they are unable to flow back into the reactor. Alcohol is passed through the reactor until the required degree of reaction is obtained. This can readily be determined, for example, by gas-chromatographic analysis of the reaction mixture. In general, two liquid phases which are constantly mixed by convection and by the ascending alcohol actually exist while alkylation is being carried out in the reactor.

However, the presence or development of two liquid phases on completion of alkylation, of which the lower phase contains the catalyst and the upper phase the reaction product, is essential for carrying out the process. The upper phase is substantially free from phosphoric acid.

On completion of alkylation, the reaction temperature is reduced to a temperature at least to 10°C below the boiling point of the reaction mixture, preferably to a temperature between 80° and 180°C, depending upon the boiling point of the reaction mixture.

The upper phase, which mainly contains the reaction product, can then be run-off in known manner. More aromatic amine can be added to the catalyst-containing phase left in the reaction tube, and the reaction with the corresponding alcohol repeated. The reaction and separation of the reaction product can of course also be carried out under slightly elevated pressure, for example at a pressure of up to about 10 atms and preferably at a pressure of up to about 3 atms.

The reaction can also be carried out continuously with advantage. For example, an outlet for the liquid reaction mixture can be arranged at the upper end of the reaction tube. The liquid reaction mixture issuing from that outlet is then passed through a separation vessel, in which the two phases separate and which is preferably heated, because the phase containing the catalyst becomes viscous on cooling. The lower phase is returned from the separation vessel into the reactor, whilst the upper phase containing the reaction product is run-off. The aromatic amine and alcohol reactants are continuously pumped in at the lower end of the reactor which is filled with phosphoric acid or even with a catalyst phase containing phosphoric acid and aromatic amine.

In general, the reaction is exothermic and the reactor is heated or cooled according to its size, the reaction velocity, heat transfer and other important parameters. It can be of advantage to introduce the amine reactant in liquid form, after melting if necessary. The alcohol can be introduced in the liquid or gas phase. Amine and alcohol can of course actually be mixed outside or inside the reactor. It is also possible to heat both reaction components before they are introduced into the reactor to such a temperature that there is no need to apply or dissipate heat to maintain the required reaction temperature. The apparatus as a whole derives from the prior art.

It can be of advantage, especially when the process is carried out continuously, to stop the reaction before it is complete, for example by applying less than the theoretically required amount of alcohol, so that the phase containing the reaction product which is run-off contains, in addition to the reaction product, unreacted amine and, in the case of dialkylation, also monoalkylated amine. Separation can then be carried out in known manner. Unreacted amine and monoalkylated amine, if any, can be recycled to the reactor. It is also possible by suitably selecting the conditions to adjust a constant ratio between monoalkylated and dialkylated amine in order to meet any existing demand for this particular product ratio, which can also be of advantage.

The process according to the invention is particularly suitable for the N-methylation and N-ethylation of aromatic amines and can be used with advantage for the production of corresponding N,N-dialkylamines and N-alkyldiphenylamines which are valuable intermediate products for the production of plant-protecting agents and dyes.

The process according to the invention has numerous advantages over the prior art. Since the product of alkylation is separated from the reaction mixture in the form of a liquid phase and not by distillation, both the reaction temperature and the temperature at which the alkylation product is separated off from the phase containing the phosphoric acid, can be lower than the boiling point of the alkylation product. This is particularly advantageous in the case of alkylation products with high boiling points. Nuclear alkylation, the re-elimination of alkyl groups from the nitrogen and other secondary reactions can thus be avoided. The possibility of rapid working up and more effective utilization of the reaction volume or, in other words, the possibility of reacting larger quantities in a smaller reaction volume, is of particular advantage. Through the development of a liquid 2-phase system, the product of alkylation is substantially free from the phosphoric acid used as catalyst, so that there is no need for expensive separation.

No alkylated aromatic amines obtainable according to this application are intermediates for preparing dyestuffs (see Ullmann, Encyclopaedie der technischen Chemie, Volume 3, third edition, page 652 (1953)).

EXAMPLES

The tests described in the following Examples were all carried out with the same reaction apparatus which consisted of a 2 liter three-necked flask to the bottom of which was attached a 5 cm diameter, 1 meter long tube which served as the reaction tube and which was heated by means of an oil bath. A thin pipe was introduced through one of the necks down to the bottom of the reaction tube and was used for introducing the alcohol. The second neck was provided with a column with an ascending air condenser adjoined at its upper end by a bridge with a descending condenser and a receiver for condensing and removing the excess alcohol distilling over and the water of reaction. The third neck was used for filling and emptying the reaction tube.

The apparatus was operated in such a way that the vapours passing over in the bridge to the descending condenser had a temperature of around 80° to 90°C, adjusted by regulating the cooling effect of the ascending condenser. The oil bath and reaction tube were kept at the temperature quoted in the following Examples.

A standard commercial 85 % by weight aqueous phosphoric acid was used for all the Examples.

EXAMPLE 1

The reaction apparatus was filled with 2 kg (21.5 mol) of aniline and 400 g (3.47 mol) of phosphoric acid. Methanol was introduced at a rate of 100 ml per hour; after heating the temperature in the reaction tube was maintained at 170° – 180°C. The introduction of methanol was stopped after 43 hours, the reaction mixture cooled to 150°C and the upper layer separated off. It consisted of 2.110 kg of dimethylaniline (99.8 %); phosphoric acid could not be detected.

The lower phase containing phosphoric acid was used as catalyst for further batches in which corresponding results were obtained.

EXAMPLE 2

2 Kg (18.7 mol) of o-tolidine and 400 g of phosphoric acid were used. Methanol was introduced at a rate of 100 ml/h for 90 hours at a reaction temperature of from 180° to 190°C. The reaction mixture was then cooled to 160°C and the reaction product run-off. 2.035 g of N,N-dimethyl-o-tolidine (99.4 %) were obtained.

EXAMPLE 3

The procedure was as in Example 2, except that m-tolidine was used instead of o-tolidine. 2.055 kg of N,N-dimethyl-m-tolidine (99.8 %) were obtained after a reaction time of 48 hours.

EXAMPLE 4

The procedure was as in Example 2, except that p-tolidine was used instead of o-tolidine. 2.045 kg of N,N-dimethyl-p-tolidone (99.8 %) were obtained after a reaction time of 60 hours.

EXAMPLE 5

The reaction apparatus was filled with 2 kg (11.8 mol) of diphenylamine and 200 g (1.74 mol) of phosphoric acid. Methanol was introduced at a rate of 50 ml/h for 40 hours at a reaction temperature of 200°C. The reaction mixture was then cooled to 140°C and the upper phase run-off. 1.822 kg of N-methyldiphenylamine (99.2 %) were obtained.

EXAMPLE 6

The procedure was as in Example 5, except that 2 kg (9.4 mol) of p-ethoxydiphenylamine were used instead of diphenylamine, and the reaction temperature was maintained at 220°C. After a reaction time of 55 hours, the reaction mixture was cooled to 120°C and the upper phase run-off. 1.85 kg of N-methyl-p-ethoxydiphenylamine (97.8 %, rest starting material) were obtained.

EXAMPLE 7

The reaction apparatus was filled with 1.6 kg (9.4 mol) of 2-aminodiphenyl and 1.000 kg (8.68 mol) of phosphoric acid. Methanol was passed through at a rate of 50 ml/h for 72 hours at a reaction temperature of 200°C. The reaction mixture was then cooled to 140°C and the upper phase run-off. 1.150 kg of 2-N,N-dimethylaminodiphenyl (96.9 %, rest 2-N-methylaminodiphenyl) were obtained.

EXAMPLE 8

The reaction apparatus was filled with 2 kg of aniline and 400 g of phosphoric acid. Ethanol was introduced at a rate of 100 ml/h at a reaction temperature of 170° to 180°C. After a reaction time of 95 hours, the reaction mixture was cooled to 100°C and the upper phase run-off. 2.280 kg of N,N-diethylaniline (99.1 %) were obtained.

EXAMPLE 9

The procedure was as in Example 8, except that 2 kg (18.7 mol) of m-tolidine were used instead of aniline, and the reaction time was increased to 110 hours. Thereafter the reaction mixture was cooled to 130°C and the upper phase runoff. 2.190 kg of N,N-diethyl-m-tolidine (98.7 %, rest N-ethyl-m-tolidine) were obtained.

EXAMPLE 10

The procedure was as in Example 9, except that 2 kg of p-tolidine were used instead of m-tolidine. In this case, the reaction time was 132 hours. Thereafter the reaction mixture was cooled to 150°C and the upper phase run-off. 2.202 kg of N,N-diethyl-p-tolidine (99.0 %, rest N-ethyl-p-tolidine) were obtained.

EXAMPLE 11

The reaction apparatus was filled with 2 kg (18.7 mol) of o-tolidine and 200 g of phosphoric acid. Ethanol was introduced at a rate of 100 ml/h for 48 hours at a reaction temperature of around 185°C. Thereafter the reaction mixture was cooled to 150°C and the upper phase run-off. 2.015 kg of a reaction product having the following composition were obtained:
20.0 % by weight of o-tolidine
72.4 % by weight of N-ethyl-o-tolidine
7.6 % by weight of N,N-diethyl-o-tolidine

EXAMPLE 12

The procedure was as in Example 11, except that 2 kg of m-tolidine were used instead of o-tolidine. After ethanol had been introduced for 32 hours, the reaction mixture was cooled to 160°C and the upper phase run-off. 2.003 kg of a reaction product having the following composition were obtained:
30 % by weight of m-tolidine
63 % by weight of N-ethyl-m-tolidine
7 % by weight of N,N-diethyl-m-tolidine

EXAMPLE 13

The procedure was as in Example 11, except that p-tolidine was used instead of o-tolidine. After ethanol had been introduced for 56 hours, the reaction mixture was cooled to 120°C and the upper phase run-off. 2.075 kg of a reaction product having the following composition were obtained:
15.7 % by weight of p-tolidine
70.3 % by weight of N-ethyl-p-tolidine
14.0 % by weight of N,N-diethyl-p-tolidine

EXAMPLE 14

The reaction apparatus was filled with 2 kg (15.7 mol) of m-chloraniline and 400 g of phosphoric acid. Methanol was introduced at a rate of 100 ml/h at a reaction temperature of 190° to 195°C. After a reaction time of 30 hours, the reaction mixture was cooled to 140°C and the upper phase run-off. 1.983 kg of N,N-dimethyl-m-chloraniline (99.6 %) were obtained.

EXAMPLES 15 and 16

In these Examples, which illustrate continuous working, the apparatus used in Examples 1 to 14 was modified to the extent that an outlet through which the reaction mixture issued into a separation vessel kept at 170°C was arranged at the lower end of the three-necked flask, but at a higher level than the reaction tube. The dimensions of this separation vessel were such that the lower catalyst phase was able to separate and flow back continuously through a similarly heated pipe into the reaction apparatus, whilst the upper phase containing the reaction product also ran off continuously after separating.

EXAMPLE 15

The apparatus was filled with a mixture of 1.400 kg (12.15 mol) of phosphoric acid, 0.900 kg (9.68 mol) of aniline and 0.600 kg (5.62 mol) of N-methylaniline. The temperature of the reaction tube was kept at 175° to 180°C, whilst 300 g/h of a mixture of 66 % by weight of aniline and 34 % by weight of methanol were pumped in. The reaction product flowing off had the following composition:

| After days | N-methylaniline | N,N-dimethylaniline |
|---|---|---|
| 1 | 38.5 % by weight | 16.4 % by weight |
| 2 | 43.4 " | 15.1 " |
| 3 | 39.9 " | 20.2 " |
| 4 | 37.0 " | 21.7 " |
| 5 | 37.6 " | 19.4 " |
| 6 | 37.6 " | 19.4 " |

EXAMPLE 16

The reaction apparatus was filled with 1.5 kg (13.03 mol) of phosphoric acid, 0.750 kg (5.56 mol) of N-ethyl-o-tolidine and 0.750 kg (7.05 mol) of o-tolidine. The reaction temperature was kept at 194° to 197°C, whilst 500 g/h of a mixture of 45 % by weight of o-tolidine and 55 % by weight of ethanol were pumped in. The reaction product had the following composition:

| After days | N-ethyl-o-tolidine | N,N-diethyl-o-tolidine |
|---|---|---|
| 1 | 67.3 % | 10.3 % |
| 2 | 67.1 % | 14.1 % |
| 3 | 65.8 % | 15.8 % |
| 4 | 64.7 % | 12.2 % |

What is claimed is:
1. Process for preparing N-alkylated aromatic amines which comprises heating in the liquid phase an aromatic amine having the formula:

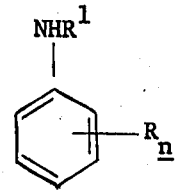

wherein
R is selected from the group of halogen, lower alkyl, alkoxy, alkylmercapto and phenyl optionally substituted by lower alkyl, alkoxy and alkylmercapto;
$R^1$ is selected from the group of hydrogen, lower alkyl, phenyl and aminophenyl optionally substituted by lower alkyl, alkoxy and arylmercapto; and
n is 0, 1, 2 or 3
together with a lower aliphatic alcohol in the presence of from 0.01 to 1.0 mol of phosphoric acid per nitrogen equivalent at a temperature in the range of from 150° to 280°C, obtaining at least two liquid phases including a lower phase which contains said phosphoric acid and thereafter separating the liquid phases formed to isolate the N-alkylated aromatic amine.

2. Process of claim 1 wherein the aromatic amine is selected from the group of aniline, o-tolidine, m-tolidine, p-tolidine, xylidines, 2-methoxydiphenylamine, 4-methoxydiphenylamine, 4-ethoxydiphenylamine and 2-aminodiphenyl.

3. Process of claim 1 wherein the reaction takes place at a temperature of from 150° to 280°C.

4. Process of claim 1 wherein the reaction takes place at a temperature of 180° to 210°c.

5. Process of claim 1 wherein the amount of phosphoric acid used is from 0.05 to 0.5 mol per nitrogen equivalent.

6. Process of claim 1 wherein the temperature of the reaction mixture is reduced, after the reaction has been completed, to a temperature of at least 10°C below the boiling point of the reaction mixture prior to separating the liquid phase.

7. Process of claim 1 wherein the phosphoric acid containing liquid phase is reused in a further alkylation reaction.

* * * * *

UNITED STATES PATENT AND TRADEMARK OFFICE
CERTIFICATE OF CORRECTION

PATENT NO. : 3,969,411
DATED : July 13, 1976
INVENTOR(S) : Joachim Schneider

It is certified that error appears in the above–identified patent and that said Letters Patent are hereby corrected as shown below:

Example 11, line 3, change "100" to --110--.

Signed and Sealed this

Fifteenth Day of February 1977

[SEAL]

Attest:

RUTH C. MASON
*Attesting Officer*

C. MARSHALL DANN
*Commissioner of Patents and Trademarks*